US006859661B2

(12) United States Patent
Tuke (10) Patent No.: US 6,859,661 B2
(45) Date of Patent: Feb. 22, 2005

(54) SURGICAL SYSTEM FOR USE IN THE COURSE OF A KNEE REPLACEMENT OPERATION

(75) Inventor: Michael Antony Tuke, Guildford (GB)

(73) Assignee: Finsbury (Development) Limited, Leatherhead (GB)

( * ) Notice: Subject to any disclaimer, the term of this patent is extended or adjusted under 35 U.S.C. 154(b) by 87 days.

(21) Appl. No.: 10/055,415

(22) Filed: Jan. 23, 2002

(65) Prior Publication Data

US 2002/0115934 A1 Aug. 22, 2002

(30) Foreign Application Priority Data

Jan. 25, 2001 (GB) .............................................. 0101990

(51) Int. Cl.[7] ................................................ A61B 5/05
(52) U.S. Cl. ....................... 600/424; 600/426; 600/427; 606/130
(58) Field of Search ................... 606/90, 130; 600/424, 600/426, 427, 473, 595

(56) References Cited

U.S. PATENT DOCUMENTS

| 5,611,353 | A | * | 3/1997 | Dance et al. ................ 600/595 |
| 6,385,475 | B1 | * | 5/2002 | Cinquin et al. ............. 600/407 |
| 6,533,737 | B1 | * | 3/2003 | Brosseau et al. ........... 600/595 |
| 6,551,325 | B2 | * | 4/2003 | Neubauer et al. ............. 606/88 |

* cited by examiner

Primary Examiner—Shawna J. Shaw
(74) Attorney, Agent, or Firm—Senniger Powers (57) ABSTRACT

A system for use by a surgeon during a knee replacement operation comprises a navigation computer whose memory holds data relating to size and shape of at least one implant as well as data obtained during pre-operative scanning. The system also registers the three dimensional position and orientation of the patient's tibia and/or femur during the course of the knee replacement operation. The system is capable of applying tension to the ligaments of the patient's knee in flexion or in extension after resection of the patient's tibia. Moreover the computer is programmed to display images of the bones on the computer's screen at different stages of the operation and with potential planes of cut.

12 Claims, 6 Drawing Sheets

SURGICAL SYSTEM FOR USE IN THE COURSE OF A KNEE REPLACEMENT OPERATION

This invention relates to a surgical system, more particularly to a surgical system and apparatus for use in the course of a knee replacement operation.

Navigation and robot systems are becoming an increasingly interesting area of technology in use for knee replacement. Several systems exist for navigation of the knee to aid alignment of the standard total knee bone cuts. In use of such systems the first step is for the patient to be scanned pre-operatively using computer aided tomography (or CT) techniques. In this way the three dimensional "form" of the patient's bones is stored in a computer's memory. In addition three dimensional data for the knee implant to be used by the surgeon, or for a range of possible knee implants which could be used by the surgeon, is also stored in the computer's memory.

During the knee replacement operation an image of the bones is displayed on a computer screen to the surgeon who has control of the computer at the operating table. A process to register the patient's actual bones from particular landmarks is undertaken which allows sensors fixed to the bones to coordinate the screen image with the patient. Bone cuts can then be made to suit the implant after sizing and judging the positions of the components on the computer screen.

A basic technique thus provides that each of the components of the implant has controlled orientation relative to the bone onto which it will be implanted. This "landmark" technique replicates most existing systems for knee replacement that do not involve such a computer.

Without a computer the sizing and positioning are done with relatively simple alignment fixtures. Thus, the navigation computer is adding little other than time and cost to the process.

Some systems can go on to so called "robot" cutting of the bones from the data available.

The known navigation process does not allow for correctly positioning the components such that the patient's soft tissues are correctly balanced in the two vitally important aspects required in successful total knee replacement. The first is to ensure that, at full extension of the knee, the medial and lateral tissues are correctly tensioned in an anatomically aligned knee. The second aspect is to ensure that the implants are chosen for size and positioned on the skeleton to ensure the correct balance of soft tissue tensions in both the extended and flexed knee.

There is therefore a need for a surgical apparatus for enabling computer navigation during a knee replacement operation which enables the surgeon to ensure that, at full extension of the knee, the medial and lateral tissues are correctly tensioned in an aligned knee. In addition there is a need to provide a surgical apparatus which will enable a surgeon to select, using a navigation computer, an implant having optimum dimensions and to implant this in optimal fashion in the patient's skeleton so as to ensure that there is the correct balance of soft tissue both in the extended knee and in the flexed knee.

The invention accordingly seeks to provide a navigation apparatus which will enable a surgeon to ensure that, at full extension of the knee, the medial and lateral tissues are correctly tensioned in an aligned knee. In addition the invention seeks to provide a surgical apparatus which will enable a surgeon to select, using a navigation computer, an implant having optimum dimensions and to implant this in optimal fashion in the patient's skeleton so as to ensure that there is the correct balance of soft tissue both in the extended knee and in the flexed knee.

The invention accordingly provides a system for use by a surgeon during implantation in a patient of a tibial implant and of a femoral implant in the course of a knee replacement operation, the system comprising:

a computer having memory for holding data relating to size and shape of at least one tibial implant and at least one femoral implant as well as data obtained during pre-operative scanning of the patient relating to the tibia and femur of the patient and also data relating to the three dimensional position and orientation of at least one bone selected from the patient's tibia and the patient's femur obtained during the course of the knee replacement operation;

display means for displaying images derived from data held in the memory of the computer relating to the patient's tibia, to the patient's femur, to the at least one tibial implant, and to the at least one femoral implant;

registration means for registering the three dimensional position and orientation of the at least one bone during the course of the knee replacement operation;

detector means connected to the computer and operatively coupled to the registration means for detecting the position and orientation of the at least one bone and for supplying to the memory of the computer data relating to the three dimensional position and orientation of at least one bone selected from the patient's tibia and the patient's femur obtained during the course of the knee replacement operation; and tensor means for applying tension to the ligaments of the patient's knee in flexion or in extension;

the computer being programmed to display on the display means, inter alia, one or more of the following images derived from data held in the memory of the computer and depicting the position and orientation of:
  (i) the patient's tibia and the patient's femur with the knee tensed by the tensor means in flexion;
  (ii) the patient's tibia and the patient's femur with the knee tensed by the tensor means in extension;
  (iii) the patient's tibia and the patient's femur with the knee tensed by the tensor means in flexion and potential planes of cut for resection of the patient's femur;
  (iv) the patient's tibia and the patient's femur with the knee tensed by the tensor means in extension and potential planes of cut for resection of the patient's femur;
  (v) the patient's tibia and the patient's femur with the knee tensed by the tensor means in flexion and with at least one component selected from the tibial component and the femoral component as it will appear after implantation thereof; and
  (vi) the patient's tibia and the patient's femur with the knee tensed by the tensor means in extension and with at least one component selected from the tibial component and the femoral component as it will appear after implantation thereof.

In a preferred system according to the invention the registration means comprises first marker means for attachment to the patient's tibia, second marker means for attachment to the patient's femur, and pointer means for touching significant features on the patient's tibia and femur, the first marker means, the second marker means, and the pointer means being all adapted for operative coupling to the detector means. In such a system the detector means can comprise an infra-red camera, while the first marker means, the second marker means, and the pointer means each carry infra-red reflector means. Alternatively the detector means may comprise an ultrasonic emitter or receiver, whereas the first marker means, the second marker means, and the pointer means each carry ultrasonic reflector or emitter means.

The tensor means is adapted for effecting distraction of the patient's knee joint in the course of the knee replacement operation, either before or after resection of the patient's tibia. Thus its function is to separate the ends of the tibia and femur and to tension the ligaments of the knee. Normally it will be preferred for the tensor means to be adapted for use after resection of the patient's tibia. Thus the tensor means may comprise an inflatable balloon. Alternatively it can be a hydraulic bag, a mechanical device having two parallel motion paddles, a mechanical device having a swivelling motion top paddle, a mechanical device having separate medial and lateral top paddles, a mechanical device having one central arm on to the femur, or a mechanical device having only a medial separation.

The display means can be a conventional computer screen if the computer is supplied with a keyboard. Alternatively the display means may comprise a touch operated screen. By placing the touch operated screen in the operating room within the reach of the surgeon the computer can be under the control of the surgeon who can call up at will the images that he wishes to inspect for the purpose of monitoring the status of the knee replacement operation and for planning his next move.

The invention addresses soft tissue balancing of the knee in both flexion and extension whilst aided by the use of computer navigation and a physical distraction of the knee joint.

In another aspect the invention relates to a system for use by a surgeon during a knee replacement operation, the system comprising:
  a computer having memory for holding data relating to size and shape of at least one tibial implant and at least one femoral implant as well as data obtained during pre-operative scanning of the patient relating to the tibia and femur of the patient and also data relating to the three dimensional position and orientation of at least one bone selected from the patient's tibia and the patient's femur obtained during the course of the knee replacement operation;
  display means for displaying images derived from data held in the memory of the computer relating to the patient's tibia, to the patient's femur, to the at least one tibial implant, and to the at least one femoral implant; and
  detector means connected to the computer and operatively coupled to registration means for registering the three dimensional position and orientation of the at least one bone during the course of the knee replacement operation, the detector means supplying to the computer data relating to the three dimensional position and orientation of the at least one bone;
  the computer being programmed to display on the display means, inter alia, one or more of the following images derived from data held in the memory of the computer and depicting the position and orientation of:
    (i) the patient's tibia and the patient's femur before or after resection of the tibia with the knee tensed by a tensor means in flexion;
    (ii) the patient's tibia and the patient's femur before or after resection of the tibia with the knee tensed by a tensor means in extension;
    (iii) the patient's tibia and the patient's femur before or after resection of the tibia with the knee tensed by a tensor means in flexion and potential planes of cut for resection of the patient's femur;
    (iv) the patient's tibia and the patient's femur before or after resection of the tibia with the knee tensed by a tensor means in extension and potential planes of cut for resection of the patient's femur;
    (v) the patient's tibia and the patient's femur before or after resection of the tibia with the knee tensed by a tensor means in flexion and with at least one component selected from the tibial component and the femoral component as it will appear after implantation thereof; and
    (vi) the patient's tibia and the patient's femur before or after resection of the tibia with the knee tensed by a tensor means in extension and with at least one component selected from the tibial component and the femoral component as it will appear after implantation thereof.

The invention also extends to a computer program for controlling a computer forming part of a system for use by a surgeon during a knee replacement operation, the system comprising:
  a computer having memory for holding data relating to size and shape of at least one tibial implant and at least one femoral implant as well as data obtained during pre-operative scanning of the patient relating to the tibia and femur of the patient and also data relating to the three dimensional position and orientation of at least one bone selected from the patient's tibia and the patient's femur obtained during the course of the knee replacement operation;
  display means for displaying images derived from data held in the memory of the computer relating to the patient's tibia, to the patient's femur, to the at least one tibial implant, and to the at least one femoral implant; and
  detector means connected to the computer and operatively coupled to registration means for registering the three dimensional position and orientation of the at least one bone during the course of the knee replacement operation, the detector means supplying to the computer data relating to the three dimensional position and orientation of the at least one bone;
  the computer program being recorded on a recording medium and arranged to display on the display means, inter alia, one or more of the following images derived from data held in the memory of the computer and depicting the position and orientation of:
    (i) the patient's tibia and the patient's femur before or after resection of the tibia with the knee tensed by a tensor means in flexion;
    (ii) the patient's tibia and the patient's femur before or after resection of the tibia with the knee tensed by a tensor means in extension;
    (iii) the patient's tibia and the patient's femur before or after resection of the tibia with the knee tensed by a tensor means in flexion and potential planes of cut for resection of the patient's femur;
    (iv) the patient's tibia and the patient's femur before or after resection of the tibia with the knee tensed by a tensor means in extension and potential planes of cut for resection of the patient's femur;
    (v) the patient's tibia and the patient's femur before or after resection of the tibia with the knee tensed by a tensor means in flexion and with at least one component selected from the tibial component and the femoral component as it will appear after implantation thereof; and (vi) the patient's tibia and the patient's femur before or after resection of the tibia with the knee tensed by a tensor means in extension and with at least one component selected from the tibial component and the femoral component as it will appear after implantation thereof.

In order that the invention may be clearly understood and readily carried into effect a preferred embodiment thereof, and its method of use, will now be described, by way of example only, with reference to the accompanying diagrammatic drawings, wherein.

Figure 1:
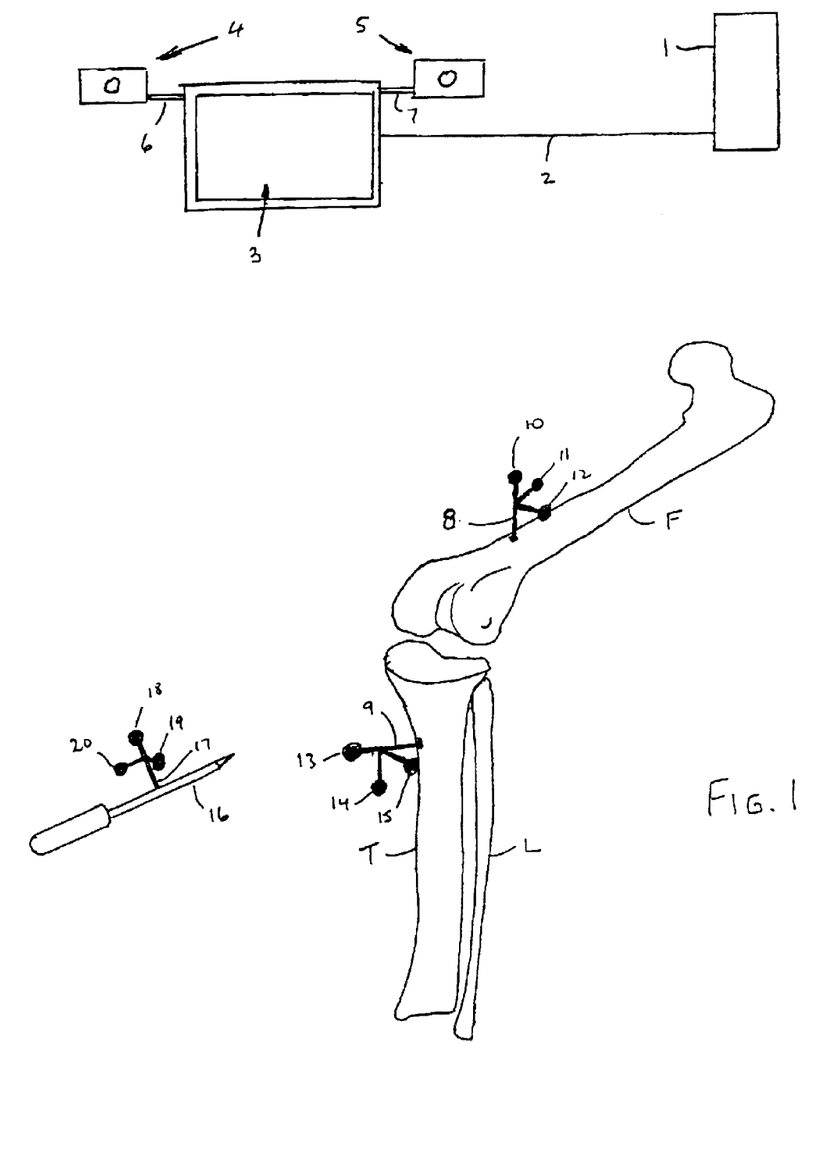
FIG. 1 is a perspective diagrammatic view of the femur and tibia of a patient undergoing a knee replacement operation and equipment in accordance with the invention which is utilised by the surgeon for effecting navigation of the knee during the operation.

Referring to the drawings, FIG. 1 illustrates a navigation computer 1 linked by a suitable lead 2 to a touch operated screen monitor 3. A pair of infra-red cameras 4, 5 are connected as indicated at 6, 7 to the screen 3. The patient's knee joint is exposed surgically in conventional fashion so as to expose the relevant portions of the patient's tibia T, and femur F. The patient's fibula L is also shown. However, the patient's tendons, blood vessels, patella, skin, fat, and muscle are not indicated in FIG. 1 or in any of the other Figures. Pins 8, 9 fitted with infra-red sensors or reflectors 10, 11, 12, 13, 14, and 15 are surgically attached to the patient's femur F and tibia T respectively. Also illustrated in FIG. 1 is a hand-held pointer 16 which is also provided with a pin 17 fitted with infra-red sensors or reflectors 18, 19, and 20.

Infra-red cameras 4, 5 map the positions of the sensors 10 to 12, 13 to 15, and 18 to 20 and the computer 1 is programmed so as to be able to display the positions of these sensors and to compute the corresponding positions of femur F and tibia T for display to the surgeon on screen 3. The computer's memory also holds images of the patient's leg obtained prior to the operation by computer aided tomography, as well as information about the available ranges of sizes of femoral and tibial components of the model of knee implant that the surgeon has decided to use.

Figure 2:
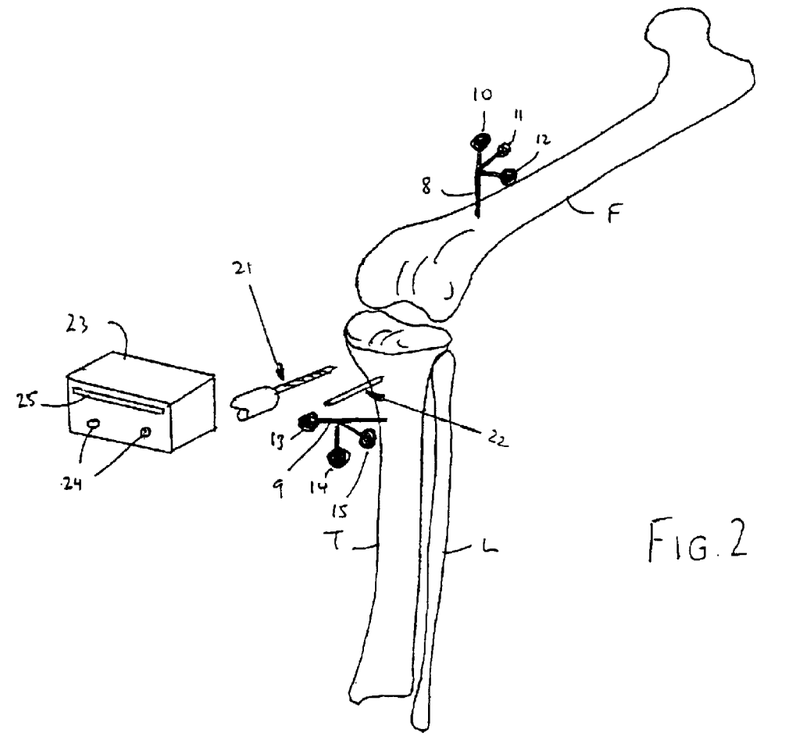
FIG. 2 is a similar view to that of FIG. 1 illustrating the affixing of a cutting block to the patient's tibia.

FIG. 2 illustrates a first stage in the knee prosthesis implantation operation. A drill 21 is used to drill holes in the patient's tibia T to receive pins 22 to hold in place a tibial cutting block 23 which has holes 24 to receive pins 22 and a slot 25 for a saw for making the tibial cut. Computer screen 3 shows on the left side an anterio-posterior view $T^a$ of the top of the patient's tibia T and, on the right hand side, a lateral view $T^l$ of the patient's tibia T. In addition screen 3 indicates at his stage of the operation the plane $P^T$ that is required by the design of femoral component of the implant selected for use by the surgeon.

Figure 3:
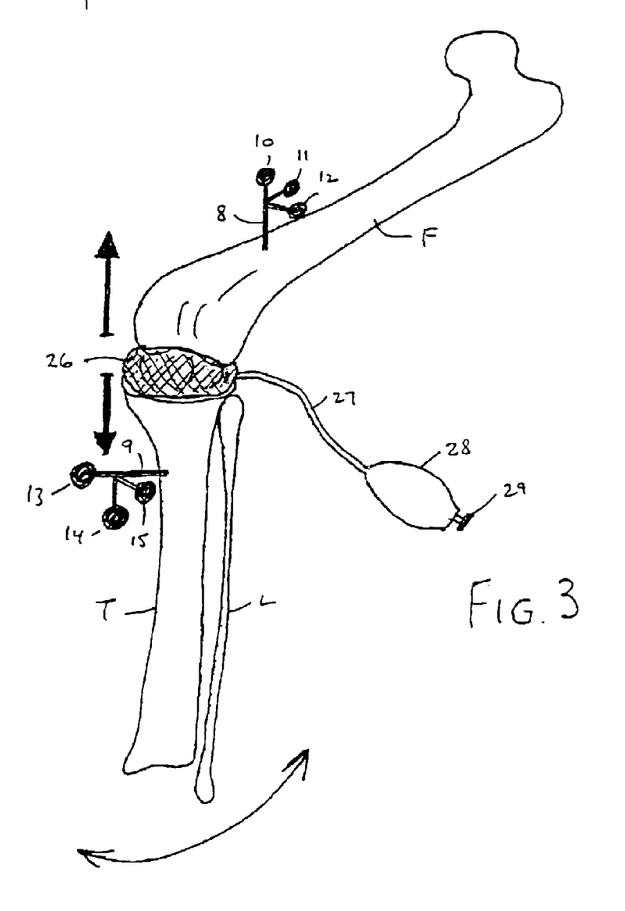
FIG. 3 is a similar view to those of FIGS. 1 and 2 illustrating physical distraction of the knee joint in flexion following the making of the tibial cut by the surgeon.

In FIG. 3 there is shown the next stage of the operation. An inflatable balloon 26 has been inserted between the patient's femur F and resected tibia T. Balloon 26 can be inflated through tube 27 by means of a hand held bulb 28 which is provided with a pressure release valve 29 by means of which the inflated balloon 26 can be deflated to permit its removal from the patient's knee joint. Screen 3 shows on the left side an anterio-posterior view of the patient's resected tibia T and femur F, while on the right side of the screen there is shown a corresponding lateral view.

Figure 4:
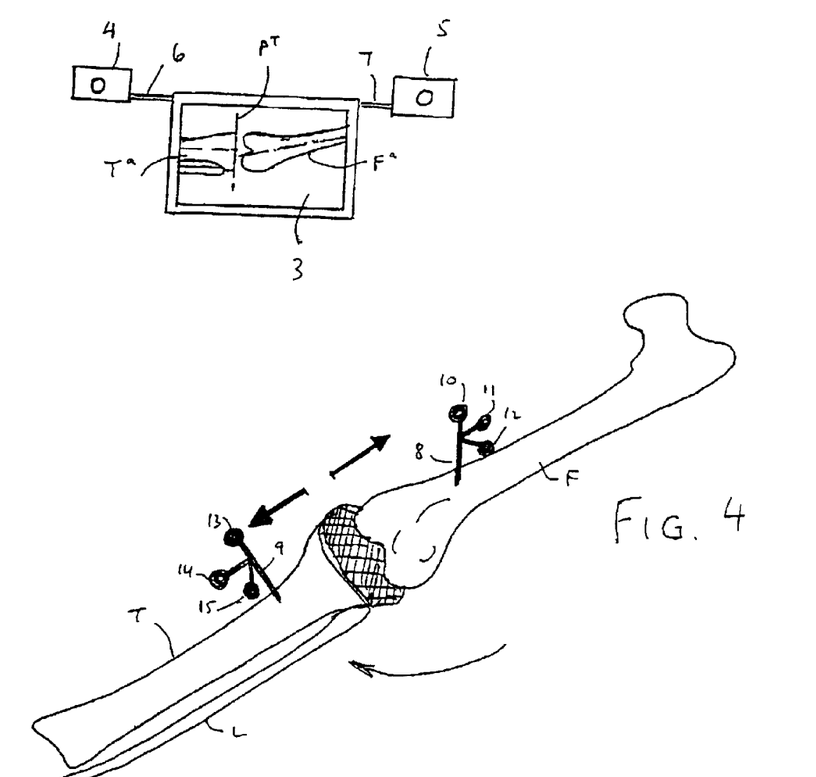
FIG. 4 is a similar view showing the knee in extension undergoing physical distraction with an anterio-posterior view on the computer screen.
Figure 5:
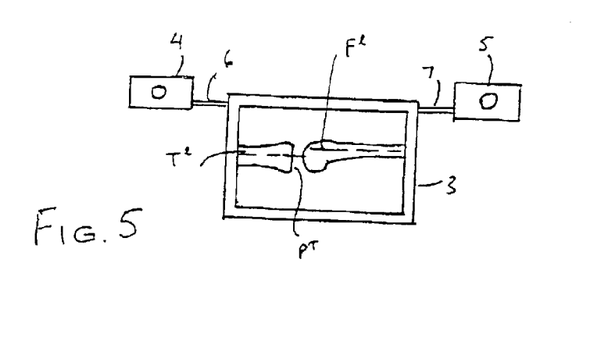
FIG. 5 is a view of the computer screen showing a lateral view of the knee corresponding to the view of FIG. 4.

FIG. 4 shows the patient's knee in extension with the inflated balloon 26 in position. Screen 3 shows an anterio-posterior view of the patient's knee joint in this condition. FIG. 5 shows screen 3 displaying the patient's knee in lateral view corresponding to FIG. 4.

Figure 6:
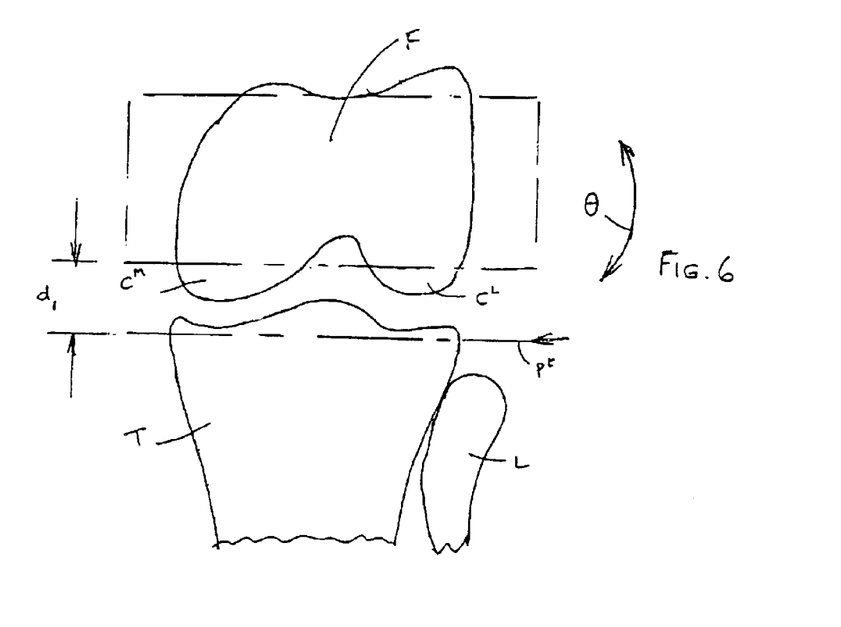
FIG. 6 is computer screen view showing an anterio-posterior view of the patient's knee in flexion.

In FIG. 6 there is shown the screen display on an enlarged scale indicating the tibia-femur space $d_1$ on an anterio-posterior view of the patient's knee in flexion after the surgeon has made the tibial cut $P^T$. The amount of permissible rotation of the femur is indicated by θ in FIG. 6. The plane of the already made tibial cut $P^T$ is also shown in FIG. 6. As will be appreciated by those skilled in the art, by rotating the femur F, the spacing at the medial condyle $C^M$ and the lateral condyle $C^L$ can be adjusted by appropriate rotation of the patient's femur F. Also indicated in FIG. 6 is a possible plane $F^A$ for the anterior femoral cut to be made by the surgeon and a possible position for the posterior cut $F^P$ to be made by the surgeon in the patient's femur.

Figure 7:
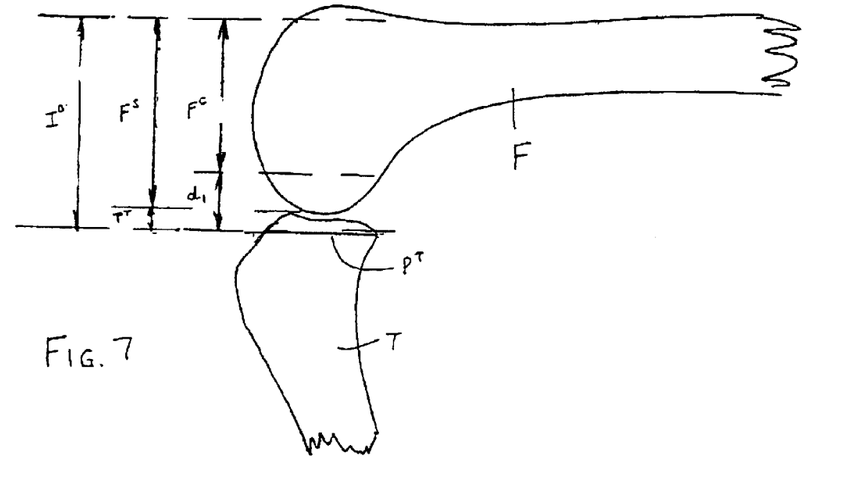
FIG. 7 is a lateral view corresponding to that of FIG. 6.

FIG. 7 shows a lateral view corresponding to that of FIG. 6. In this view there are included the overall implant size $I^O$, the tibia thickness assessment $T^T$, the tibia-femur space $d_t$, and the femur cut size $F^C$. These lines are added to the display by the computer program which uses the data loaded into the navigation computer's memory for this purpose.

Figure 8:
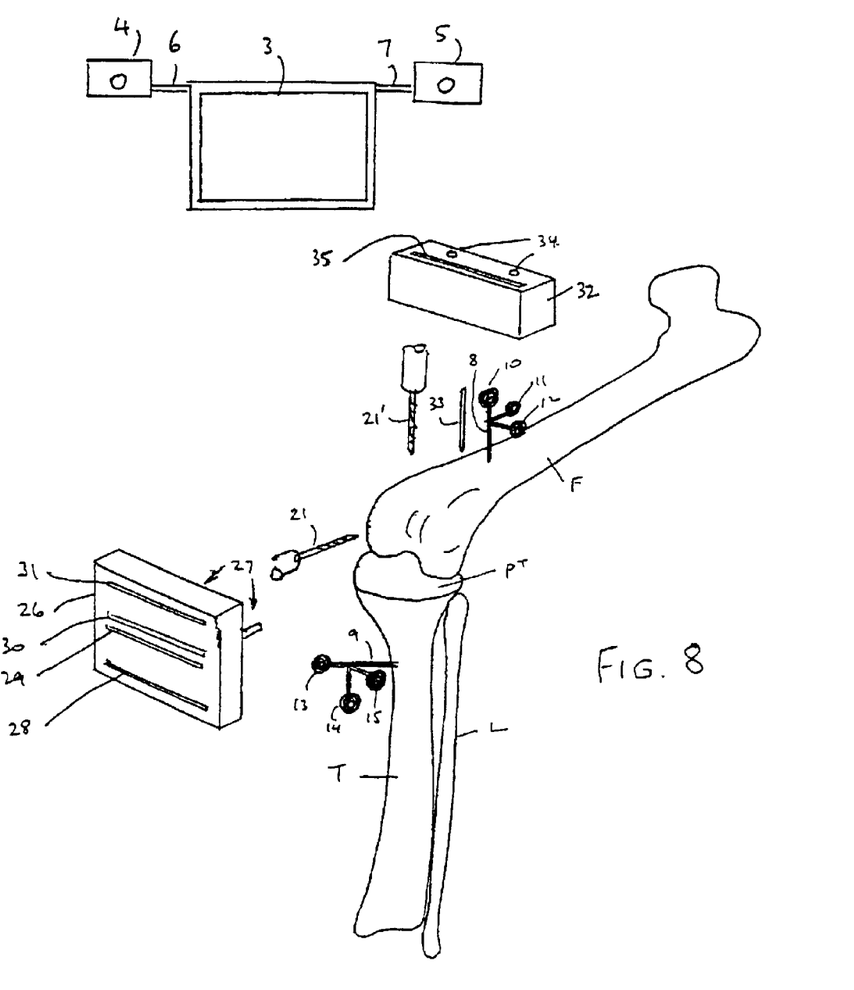
FIG. 8 illustrates the affixing of cutting blocks to the femur for making the necessary cuts to accommodate the selected femoral component of the knee prosthesis.

In FIG. 8 there is shown a further view of the patient's knee in the flexed position, illustrating how the surgeon uses the drill 21 to attach temporarily to the patient's femur F a cutting block 26 which is located in position on the patient's femur by means of pins 27, only one of which is visible in FIG. 8. Block 26 is provided with slots 28, 29, 30 and 31 by means of which the surgeon can make the planned anterior cut $F^A$ and the planned posterior cut $F^P$.

Having made the anterior cut $F^A$ and the posterior cut $F^P$, the surgeon can then fit a further cutting block 32 to the patient's femur F, using drill 21 (as indicated at 21') to drill holes for pins 33 which are received in holes 34 in block 32. During this part of the operation block 26 is still in place on the patient's femur F and is used as a guide to position the block 32. Slot 35 in block 32 permits the surgeon to make the distal cut in the patient's femur F.

The system of the invention can be used in the following manner:

1. The patient's leg is CT scanned and entered into the memory of the navigation computer 1 in the normal way provided by the systems available.
2. The knee is exposed in the normal way including removal of osteophytes and obvious soft tissue adhesions. The anterior cruciate is divided, if present, assuming that the intended implant cannot accommodate this ligament. The posterior cruciate ligament may be resected also at the choice of the surgeon.
3. The navigation landmarks for the end of the femur, the end of the tibia and the patella are registered as normal practice with the relevant system. For this purpose the surgeon can affix pins 8 and 9 to the patient's femur F and tibia T respectively and register pins 8 and 9 using pointer 16 and the markers 18 to 20 mounted thereon to indicate by means of the infra-red cameras 4 and 5 to the computer 1 the position of pins 8 and 9 in relation to the infra-red cameras 4 and 5. The infra-red cameras 4 and 5 can then track markers 10 to 12, 13 to 15, and 18 to 20, while computer 1 stores the relevant data provided by cameras 4 and 5 to permit the position and orientation of the tibia T and femur F to be displayed on the computer screen 3. This step is illustrated in FIG. 1.

4. The computer 1 is then used to evaluate the tibia resection by establishing the plane $P^T$ that is required by the implant, e.g. a 7° posterior slope, and to cut just below the principal defect. If there is little erosion, the plane $P^T$ is set at about 4 mm below the medial condyle $C^M$. Cutting block 23 is positioned and fixed onto the tibia T using the computer 1 and its navigation process and the tibia T resected, as indicated in FIG. 2. Hence pointer 16 can be moved over the surface of tibia T and femur F until its position in the image on the computer screen 3 corresponds to the correct position for the tibial cut to be made on the plane $P^T$. Alternatively, a robot driven by the computer 1 may be used to resect the tibia T on the chosen plane $P^T$.

5. The knee is explored posteriorly for adhesions on the femur F and tibia T especially if there was any kind of fixed deformity, such as flexion, valgus or varus.

6. A physical spacer, such as inflatable balloon 26, is applied to the flexed knee, as illustrated in FIG. 3, so that it is tensed gently but sufficiently to open the knee on the medial side to achieve the degree of tension (A-P drawer) that is closest to the normal knee tested this way. Instead of using inflatable balloon 26, other forms of physical spacer or tensor can be used. Thus, for example, a hydraulic bag could be used in place of inflatable balloon 26. Alternatively it could be a mechanical device having two parallel motion paddles, or a swivelling motion top paddle, or separate medial and lateral top paddles, or one central arm on to the femur, or only a medial separation. In use of any of these physical spacers, the physical spacer should be designed so as to be able to be locked in the desired open position. The spacer preferably also has a measurement scale to allow a direct reading of the gap obtained; this may optionally be linked into the computer 1 for display and/or for use as part of the further surgical procedure to be described below.

7. The navigation computer 1 is then consulted, as indicated in FIGS. 4 and 5, for the space $d_1$ (see FIG. 6) between the bones as recorded by the spacer 26 to verify one against the other. The flexion angle of the knee is adjusted to achieve a parallel line between the anterior femur as viewed from the side and the cut tibia. The computer view with alignment lines as illustrated in FIGS. 6 and 7 can assist in this.

8. A distal view onto the femur, as illustrated in FIG. 6, is then chosen on the computer screen 3 and the rotation θ of the femur F assessed. If the implant design requires, or the surgeon chooses, a particular external rotation, the computer 1 can be adjusted to make such allowance. Alternatively the spacer 26 can be adjusted to register the chosen rotation on the computer screen 3 again using lines or angles displayed.

9. This flexion position is locked into the computer memory with particular attention to the relative three dimensional orientations and positions of the femur F and tibia T.

10. The tensor 26 is released, the knee fully extended and the tensor 26 reinserted into the knee and tensioned again. The tensor 26 in this position is preferably free to allow the leg alignment to be dictated by the patient's ligaments. If a mechanical spacer is used, it should rotate between its two paddles, one on the tibia T and the other on the distal femur F. Alternatively, two paddles could independently sit onto the femoral condyles $C^M$ and $C^L$, or one could sit between the condyles $C^M$ and $C^L$.

11. In this position with the knee "tensed" it should feel stable. The computer 1 can now be consulted to assess full extension which should be adjusted on the patient, if necessary. The valgus/varus alignment is then checked on the computer screen 3. If there is a valgus or varus deformity between the normal alignment of hip, knee and ankle centre it will be seen on the computer alignment. Any such deformity can be checked against the contra-lateral leg if it is regarded as normal. Any unsatisfactory alignment indicates fixed soft tissues that will require a soft tissue release procedure. This may be performed with the spacer 26 removed, then the alignment should be re-assessed with the spacer 26 replaced. The tight tissues may be palpated whilst the spacer 26 is in place. The computer 1 may be programmed to display a help screen to show the most likely and best sequence of tissue releases to be made.

12. Once the alignment is satisfactory and full extension is confirmed with the spacer 26 in place and providing a stable leg the computer 1 again is instructed to record the orientations in three dimensions of the femur F and the tibia T.

13. The knee can now be relaxed and the navigation computer 1 consulted to choose the optimum implant configuration for this patient. The two positions recorded above relate to the bone orientations, positions, and their relative positions in flexion and extension. The computer 1 also knows the implant geometry, and component thicknesses. With this information the component sizes can be calculated and the three dimensional positions of both the femoral implant and also the tibial implant easily fixed. The surgeon's judgement will be required to help in this process with options, for example on adjusting the femur anterior/posterior (AP) size $I^O$ and tibia thickness $T^T$. For this purpose the computer 1 can be programmed to follow the following sequence of steps:

(a) The femur F is sized from the anterior cortex to the posterior condyles, via a template or dimensions of the different sizes of femoral implant available; a lateral and distal view can be displayed on one screen and the size and position in both planes chosen.

(b) The lateral view of the femur and the femoral component in this position will then be used with the tibia in its tensed position to size the tibial component thickness $T^T$.

(c) This tibial component thickness $T^T$ will then be modelled on the tibia T in the extended tensed knee view and the femoral component position adjusted proximally/distally to fit the extended space.

(d) These steps are stored in the memory of computer 1 and complete the choice and position of the tibial and femoral components with relation to fully balancing the two important elements in replacing the knee.

14. The femur cuts can then be made with the aid of computer 1 by navigation and/or using a robot to suit the relevant femoral and tibial components.

15. The spacer 26 can be used again after making the cuts to confirm the process of "balancing" and alignment on the computer 1. This may be especially useful if a considerable fixed deformity was present. In this instance, preliminary cuts could be made to help perform releases. The computer 1 could be used to indicate safe preliminary cut levels.

16. Tibia and femur implant fixation holes or features can be fixed from the navigation system. By again fitting the spacer 26, or fitting a tibia trial without fixation features and a femur trial, the extension, flexion and deep flexion positions can be assessed on the computer screen 3 and the ideal tibia position fixed.

17. The fixation holes or features, for example, the holes for pins 22 and 33, can then be made in the bone by computer navigation positioning of an instrument, or by robot.

18. The implants chosen by the computer 1 can be trialed for confirmation and fixed in the usual way.

19. The freedom between the components, leg alignment, and three dimensional positions can be further assessed on the computer screen 3 at this stage, recorded in the memory of computer 1, and used for further analysis. This method should ensure that the two trialed positions with the physical spacer 26 in flexion, then extension, and as recorded by the navigation computer 1, are reproduced with the implant.

What is claimed is:

1. A system for use by a surgeon during implantation in a patient of a tibial implant and of a femoral implant in the course of a knee replacement operation, the system comprising:

a computer having memory for holding data relating to size and shape of at least one tibial implant and at least one femoral implant as well as data obtained during pre-operative scanning of the patient relating to the tibia and femur of the patient and also data relating to the three dimensional position and orientation of at least one bone selected from the patient's tibia and the patient's femur obtained during the course of the knee replacement operation;

display means for displaying images derived from data held in the memory of the computer relating to the patient's tibia, to the patient's femur, to the at least one tibial implant, and to the at least one femoral implant;

registration means for registering the three dimensional position and orientation of the at least one bone during the course of the knee replacement operation;

detector means connected to the computer and operatively coupled to the registration means for detecting the position and orientation of the at least one bone and for supplying to the memory of the computer data relating to the three dimensional position and orientation of at least one bone selected from the patient's tibia and the patient's femur obtained during the course of the knee replacement operation; and tensor means for applying tension to the ligaments of the patient's knee in flexion in extension;

the computer being configured to display on the display means, at least one more of the following images derived from data held in the memory of the computer and depicting the position and orientation of:

(i) the patient's tibia and the patient's femur prior to resection of the femur with the knee tensed by the tensor means in flexion;

(ii) the patient's tibia and the patient's femur prior to resection of the femur with the knee tensed by the tensor means in extension;

(iii) the patient's tibia and the patient's femur prior to resection of the femur with the knee tensed by the tensor means in flexion and potential planes of cut for resection of the patient's femur;

(iv) the patient's tibia and the patient's femur prior to resection of the femur with the knee tensed by the tensor means in extension and potential planes of cut for resection of the patient's femur;

(v) the patient's tibia and the patient's femur prior to resection of the femur with the knee tensed by the tensor means in flexion and with at least one component selected from the tibial component and the femoral component as it will appear after implantation thereof; and (vi) the patient's tibia and the patient's femur prior to resection of the femur with the knee tensed by the tensor means in extension and with at least one component selected from the tibial component and the femoral component as it will appear after implantation thereof.

2. A system according to claim 1, wherein the registration means comprises first marker means for attachment to the patient's tibia, second marker means for attachment to the patient's femur, and pointer means for touching significant features on the patient's tibia and femur, and wherein the first marker means, the second marker means, and the pointer means are all adapted for operative coupling to the detector means.

3. A system according to claim 2, wherein the detector means comprises an infra-red camera, and wherein the first marker means, the second marker means, and the pointer means each carry infra-red reflector means.

4. A system according to claim 2, wherein the detector means comprises an ultrasonic emitter or receiver, and wherein the first marker means, the second marker means, and the pointer means each carry ultrasonic reflector or emitter means.

5. A system according to claim 1, wherein the tensor means comprises an inflatable balloon.

6. A system according to claim 1, wherein the tensor means is selected from the group consisting of a hydraulic bag, a mechanical device having two parallel motion paddles, a mechanical device having a swivelling motion top paddle, a mechanical device having separate medial and lateral top paddles, a mechanical device having one central arm on to the femur, and a mechanical device having only a medial separation.

7. A system for use by a surgeon during a knee replacement operation, the system comprising:

a computer having memory for holding data relating to size and shape of at least one tibial implant and at least one femoral implant as well as data obtained during pre-operative scanning of the patient relating to the tibia and femur of the patient and also data relating to the three dimensional position and orientation of at least one bone selected from the patient's tibia and the patient's femur obtained during the course of the knee replacement operation;

display means for displaying images derived from data held in the memory of the computer relating to the patient's tibia, to the patient's femur, to the at least one tibial implant, and to the at least one femoral implant; and detector means connected to the computer and operatively coupled to registration means for registering the three dimensional position and orientation of the at least one bone during the course of the knee replacement operation, the detector means supplying to the computer data relating to the three dimensional position and orientation of the at least one bone;

the computer being configured to display on the display means, at least one or more of the following images derived from data held in the memory of the computer and depicting the position and orientation of:

(i) the patient's tibia and the patient's femur before or after resection of the tibia and prior to resection of the femur with the knee tensed by a tensor means in flexion;

(ii) the patient's tibia and the patient's femur before or after resection of the tibia and prior to resection of the femur with the knee tensed by a tensor means in extension;

(iii) the patient's tibia and the patient's femur before or after resection of the tibia and prior to resection of the femur with the knee tensed by a tensor means in flexion and potential planes of cut for resection of the patient's femur;

(iv) the patient's tibia and the patient's femur before or after resection of the tibia and prior to resection of the femur with the knee tensed by a tensor means in extension and potential planes of cut for resection of the patient's femur;

(v) the patient's tibia and the patient's femur before or after resection of the tibia and prior to resection of the femur with the knee tensed by a tensor means in flexion and with at least one component selected from the tibial component and the femoral component as it will appear after implantation thereof; and (vi) the patient's tibia and the patient's femur before or after resection of the tibia and prior to resection of the femur with the knee tensed by a tensor means in extension and with at least one component selected from the tibial component and the femoral component as it will appear after implantation thereof.

8. A computer program product having instructions contained on a computer readable medium for controlling a computer forming part of a system for use by a surgeon during a knee replacement operation on a patient, the system comprising:

a computer having memory for holding data relating to size and shape of at least one tibial implant and at least one femoral implant as well as data obtained during pre-operative scanning of the patient relating to the tibia and femur of the patient and also data relating to the three dimensional position and orientation of at least one bone selected from the patient's tibia and the patient's femur obtained during the course of the knee replacement operation;

display means for displaying images derived from data held in the memory of the computer relating to the patient's tibia, to the patient's femur, to the at least one tibial implant, and to the at least one femoral implant; and detector means connected to the computer and operatively coupled to registration means for registering the three dimensional position and orientation of the at least one bone during the course of the knee replacement operation, the detector means supplying to the computer data relating to the three dimensional position and orientation of the at least one bone;

the computer adapted to be instructed by the computer program product to display on the display means, at least one or more of the following images derived from data held in the memory of the computer and depicting the position and orientation of:

(i) the patient's tibia and the patient's femur before or after resection of the tibia and prior to resection of the femur with the knee tensed by a tensor means in flexion;

(ii) the patient's tibia and the patient's femur before or after resection of the tibia and prior to resection of the femur with the knee tensed by a tensor means in extension;

(iii) the patient's tibia and the patient's femur before or after resection of the tibia and prior to resection of the femur with the knee tensed by a tensor means in flexion and potential planes of cut for resection of the patient's femur;

(iv) the patient's tibia and the patient's femur before or after resection of the tibia and prior to resection of the femur with the knee tensed by a tensor means in extension and potential planes of cut for resection of the patient's femur;

(v) the patient's tibia and the patient's femur before or after resection of the tibia and prior to resection of the femur with the knee tensed by a tensor means in flexion and with at least one component selected from the tibial component and the femoral component as it will appear after implantation thereof; and (vi) the patient's tibia and the patient's femur before or after resection of the tibia and prior to resection of the femur with the knee tensed by a tensor means in extension and with at least one component selected from the tibial component and the femoral component as it will appear after implantation thereof.

9. A system for use by a surgeon during implantation in a patient of a tibial implant and of a femoral implant in the course of a knee replacement operation, the system comprising:

a computer having memory for holding data relating to size and shape of at least one tibial implant and at least one femoral implant as well as data obtained during pre-operative scanning of the patient relating to the tibia and femur of the patient and also data relating to the three dimensional position and orientation of at least one bone selected from the patient's tibia and the patient's femur obtained during the course of the knee replacement operation;

display means for displaying images derived from data held in the memory of the computer relating to the patient's tibia, to the patient's femur, to the at least one tibial implant, and to the at least one femoral implant;

registration means for registering the three dimensional position and orientation of the at least one bone during the course of the knee replacement operation;

detector means connected to the computer and operatively coupled to the registration means for detecting the position and orientation of the at least one bone and for supplying to the memory of the computer data relating to the three dimensional position and orientation of at least one bone selected from the patient's tibia and the patient's femur obtained during the course of the knee replacement operation; and tensor means comprising an inflatable balloon for applying tension to the ligaments of the patient's knee in flexion or in extension;

the computer being configured to display on the display means, at least one or more of the following images derived from data held in the memory of the computer and depicting the position and orientation of:
(i) the patient's tibia and the patient's femur with the knee tensed by the tensor means in flexion;
(ii) the patient's tibia and the patient's femur with the knee tensed by the tensor means in extension;
(iii) the patient's tibia and the patient's femur with the knee tensed by the tensor means in flexion and potential planes of cut for resection of the patient's femur;
(iv) the patient's tibia and the patient's femur with the knee tensed by the tensor means in extension and potential planes of cut for resection of the patient's femur;
(v) the patient's tibia and the patient's femur with the knee tensed by the tensor means in flexion and with at least one component selected from the tibial component and the femoral component as it will appear after implantation thereof; and
(vi) the patient's tibia and the patient's femur with the knee tensed by the tensor means in extension and with at least one component selected from the tibial component and the femoral component as it will appear after implantation thereof.

10. A system for use by a surgeon during implantation in a patient of a tibial implant and of a femoral implant in the course of a knee replacement operation, the system comprising:
at least one sensor for registering the three dimensional position and orientation of a bone selected from the patient's tibia and the patient's femur;
a detector for detecting the position the sensor;
a computer connected to the detector, the computer being configured for determining the three dimensional position and orientation of at least one bone selected from the patient's tibia and the patient's femur, the computer having memory for holding data relating to size and shape of at least one tibial implant and at least one femoral implant as well as data obtained during pre-operative scanning of the patient relating to the tibia and femur of the patient;
a display for displaying images derived from data held in the memory of the computer; and
a spacer for placement between the tibia and femur and applying tension to the ligaments of the patient's knee in flexion and extension;
the display displaying one or more of the following images derived from data held in the memory of the computer and depicting the position and orientation of:
(i) the patient's tibia and the patient's femur with the knee tensed by the spacer in flexion;
(ii) the patient's tibia and the patient's femur with the knee tensed by the spacer in extension;
(iii) the patient's tibia and the patient's femur with the knee tensed by the spacer in flexion and potential planes of cut for resection of the patient's femur;
(iv) the patient's tibia and the patient's femur with the knee tensed by the spacer in extension and potential planes of cut for resection of the patient's femur;
(v) the patient's tibia and the patient's femur with the knee tensed by the spacer in flexion and with at least one component selected from the tibial component and the femoral component as it will appear after implantation thereof; and
(vi) the patient's tibia and the patient's femur with the knee tensed by the spacer in extension and with at least one component selected from the tibial component and the femoral component as it will appear after implantation thereof.

11. A system for use by a surgeon during implantation in a patient of a tibial implant and of a femoral implant in the course of a knee replacement operation, the system comprising:
at least one sensor for registering the three dimensional position and orientation of a bone selected from the patient's tibia and the patient's femur;
a detector for detecting the position the sensor;
a computer connected to the detector, the computer being configured for determining the three dimensional position and orientation of at least one bone selected from the patient's tibia and the patient's femur, the computer having memory for holding data relating to size and shape of at least one tibial implant and at least one femoral implant as well as data obtained during pre-operative scanning of the patient relating to the tibia and femur of the patient;
a display for displaying images derived from data held in the memory of the computer; and
a spacer for placement between the tibia and femur and applying tension to the ligaments of the patient's knee in flexion and extension;
the spacer being selected from the group consisting of an inflatable balloon, a hydraulic bag, a mechanical device having two parallel motion paddles, a mechanical device having swivelling motion top paddle, and a mechanical device having separate medial and lateral top paddles;
the display displaying one or more of the following images derived from data held in the memory of the computer and depicting the position and orientation of:
(i) the patient's tibia and the patient's femur with the knee tensed by the spacer in flexion;
(ii) the patient's tibia and the patient's femur with the knee tensed by the spacer in extension;
(iii) the patient's tibia and the patient's femur with the knee tensed by the spacer in flexion and potential planes of cut for resection of the patient's femur;
(iv) the patient's tibia and the patient's femur with the knee tensed by the spacer in extension and potential planes of cut for resection of the patient's femur;
(v) the patient's tibia and the patient's femur with the knee tensed by the spacer in flexion and with at least one component selected from the tibial component and the femoral component as it will appear after implantation thereof; and
(vi) the patient's tibia and the patient's femur with the knee tensed by the spacer in extension and with at least one component selected from the tibial component and the femoral component as it will appear after implantation thereof.

12. A method of operating a system for use by a surgeon during implantation in a patient of a tibial implant and of a femoral implant in the course of a knee replacement operation, the method comprising:
storing data in a computer having memory relating to size and shape of at least one tibial implant and at least one femoral implant as well as data obtained during pre-operative scanning of the patient relating to the tibia and femur of the patient and also data relating to the three dimensional position and orientation of at least one bone selected from the patient's tibia and the patient's femur obtained during the course of the knee replacement operation;

registering the three dimensional position and orientation of the at least one bone during the course of the knee replacement operation;

detecting the position and orientation of the at least one bone and for supplying to the memory of the computer data relating to the three dimensional position and orientation of at least one bone selected from the patient's tibia and the patient's femur obtained during the course of the knee replacement operation; and applying tension with a tensor means to the ligaments of the patient's knee in flexion and in extension;

displaying one or more of the following images derived from data held in the memory of the computer and depicting the position and orientation of:
  (i) the patient's tibia and the patient's femur prior to resection of the femur with the knee tensed by the tensor means in flexion;
  (ii) the patient's tibia and the patient's femur prior to resection of the femur with the knee tensed by the tensor means in extension;
  (iii) the patient's tibia and the patient's femur prior to resection of the femur with the knee tensed by the tensor means in flexion and potential planes of cut for resection of the patient's femur;
  (iv) the patient's tibia and the patient's femur prior to resection of the femur with the knee tensed by the tensor means in extension and potential planes of cut for resection of the patient's femur;
  (v) the patient's tibia and the patient's femur prior to resection of the femur with the knee tensed by the tensor means in flexion and with at least one component selected from the tibial component and the femoral component as it will appear after implantation thereof; and
  (vi) the patient's tibia and the patient's femur prior to resection of the femur with the knee tensed by the tensor means in extension and with at least one component selected from the tibial component and the femoral component as it will appear after implantation thereof.

* * * * *

(12) EX PARTE REEXAMINATION CERTIFICATE (5919th)
United States Patent
Tuke (10) Number: US 6,859,661 C1
(45) Certificate Issued: Oct. 2, 2007

(54) SURGICAL SYSTEM FOR USE IN THE COURSE OF A KNEE REPLACEMENT OPERATION

(75) Inventor: Michael Antony Tuke, Guildford (GB)

(73) Assignee: Finsbury (Development) Limited, Leatherhead (GB)

Reexamination Request:
No. 90/008,206, Sep. 1, 2006

Reexamination Certificate for:
Patent No.: 6,859,661
Issued: Feb. 22, 2005
Appl. No.: 10/055,415
Filed: Jan. 23, 2002

(30) Foreign Application Priority Data

Jan. 25, 2001 (GB) ............................................ 0101990

(51) Int. Cl.
*A61B 19/00* (2006.01)
*A61B 5/05* (2006.01)
*A61F 2/38*

(52) U.S. Cl. ...................... 600/424; 600/426; 600/427; 606/130

(58) Field of Classification Search ........................ None
See application file for complete search history.

(56) References Cited

U.S. PATENT DOCUMENTS

| 5,682,886 A | 11/1997 | Delp et al. |
| 5,733,292 A | 3/1998 | Hammett et al. |
| 5,800,438 A | 9/1998 | Tuke et al. |

FOREIGN PATENT DOCUMENTS

| EP | 0720834 | 7/1996 |
| WO | 0054687 | 9/2000 |

*Primary Examiner*—David O. Reip (57) ABSTRACT

A system for use by a surgeon during a knee replacement operation comprises a navigation computer whose memory holds data relating to size and shape of at least one implant as well as data obtained during pre-operative scanning. The system also registers the three dimensional position and orientation of the patient's tibia and/or femur during the course of the knee replacement operation. The system is capable of applying tension to the ligaments of the patient's knee in flexion or in extension after resection of the patient's tibia. Moreover the computer is programmed to display images of the bones on the computer's screen at different stages of the operation and with potential planes of cut.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–12 is confirmed.

* * * * *